(12) United States Patent
Spady et al.

(10) Patent No.: US 7,295,314 B1
(45) Date of Patent: Nov. 13, 2007

(54) METROLOGY/INSPECTION POSITIONING SYSTEM

(75) Inventors: Blaine R. Spady, Lincoln, NE (US); John D. Heaton, Fremont, CA (US); Robert Buchanan, Pleasanton, CA (US); Richard A. Yarussi, San Francisco, CA (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

(21) Appl. No.: 09/458,123

(22) Filed: Dec. 8, 1999

Related U.S. Application Data

(63) Continuation-in-part of application No. 09/113,484, filed on Jul. 10, 1998, now Pat. No. 6,320,609.

(51) Int. Cl.
G01B 11/00 (2006.01)
G01B 11/14 (2006.01)
G01N 21/00 (2006.01)
G06K 9/00 (2006.01)

(52) U.S. Cl. .................. 356/401; 356/237.1; 356/614; 382/141; 382/145; 382/151

(58) Field of Classification Search ........ 356/399–401, 356/237.1–237.6, 614–616, 445–448, 630–632, 356/624, 238.1, 238.3; 382/141, 144, 145, 382/147, 148, 152, 286, 289, 291, 292, 298, 382/299, 149, 151; 250/559.01, 559.29, 250/559.3; 702/94, 95, 150–153, 38; 355/53, 355/55, 77; 430/5, 22, 30; 269/329, 63, 269/4, 55–59, 1, 3; 348/88, 82, 94, 95; 700/114, 700/186, 192–194, 257; 414/935, 936; 345/649, 345/672

See application file for complete search history.

(56) References Cited

U.S. PATENT DOCUMENTS 4,107,527 A    8/1978   Cherepin et al. ........... 250/309

(Continued)

FOREIGN PATENT DOCUMENTS

EP         0 893 203 A2    1/1999

(Continued)

OTHER PUBLICATIONS

Peter Rosenthal, "Integrated FTIR reflectometer controls semiconductor fabrication process", (Laser Focus World, Apr. 1998).

(Continued)

Primary Examiner—Gregory J. Toatley, Jr.
Assistant Examiner—Gordon J. Stock, Jr.
(74) Attorney, Agent, or Firm—Silicon Valley Patent Group LLP

(57) ABSTRACT

A metrology/inspection system moves the imaging and/or measuring equipment of the system relative to a wafer. Accordingly, measurement or inspection of the wafer does not require that the wafer be mounted on a precision stage. This allows the wafer to be at rest on any structure native in a processing apparatus when the system measures or inspects the wafer. Accordingly, measurement does not require removing the wafer from the processing apparatus and does not delay processing since the wafer can be measured, for example, during a required cool down period of device fabrication process. Alignment of an optical system includes pre-alignment base on edge detection using the optical system and more precise alignment using image recognition. An R-θ stage can position the optical system at inspection areas on the wafer. Image rotation can provide a fixed orientation for all images at the various inspection areas and can maintain the fixed orientation when moving from one inspection area to the next.

20 Claims, 10 Drawing Sheets

U.S. PATENT DOCUMENTS

| | | | | |
|---|---|---|---|---|
| 4,202,037 | A | | 5/1980 | Glaser et al. ............... 364/518 |
| 4,556,317 | A | * | 12/1985 | Sandland et al. ........ 356/237.1 |
| 4,593,406 | A | | 6/1986 | Stone .......................... 382/44 |
| 4,744,642 | A | | 5/1988 | Yoshinage et al. .......... 350/518 |
| 4,794,238 | A | * | 12/1988 | Hampton ............... 235/462.32 |
| 4,832,474 | A | | 5/1989 | Yoshinage et al. .......... 350/529 |
| 4,966,520 | A | * | 10/1990 | Yokota et al. ............... 414/816 |
| 5,127,726 | A | | 7/1992 | Moran ........................ 356/237 |
| 5,159,412 | A | | 10/1992 | Willenborg et al. ........ 356/445 |
| 5,210,410 | A | | 5/1993 | Barrett ....................... 250/234 |
| 5,238,354 | A | * | 8/1993 | Volovich .................... 414/779 |
| 5,381,004 | A | * | 1/1995 | Uritsky et al. .............. 250/307 |
| 5,474,647 | A | * | 12/1995 | Poultney et al. ............... 438/5 |
| 5,517,312 | A | | 5/1996 | Finarov ...................... 356/386 |
| 5,532,874 | A | | 7/1996 | Stein .......................... 359/394 |
| 5,546,179 | A | * | 8/1996 | Cheng ......................... 356/73 |
| 5,597,590 | A | | 1/1997 | Tanimoto et al. ........ 425/174.4 |
| 5,604,344 | A | | 2/1997 | Finarov .................. 250/201.3 |
| 5,669,979 | A | * | 9/1997 | Elliott et al. .................... 134/1 |
| 5,682,242 | A | | 10/1997 | Eylon ........................ 356/401 |
| 5,730,642 | A | | 3/1998 | Sandhu et al. ................. 451/6 |
| 5,764,365 | A | | 6/1998 | Finarov ...................... 356/381 |
| 5,867,590 | A | | 2/1999 | Eylon ......................... 382/151 |
| 5,910,846 | A | | 6/1999 | Sandhu ....................... 356/381 |
| 5,917,601 | A | | 6/1999 | Shimazaki et al. .......... 356/375 |
| 5,957,749 | A | | 9/1999 | Finarov ......................... 451/6 |
| 5,981,937 | A | | 11/1999 | Denaro ....................... 250/216 |
| 6,038,029 | A | | 3/2000 | Finarov ...................... 356/399 |
| 6,111,634 | A | | 8/2000 | Pecen et al. .................. 356/72 |
| 6,157,450 | A | * | 12/2000 | Marchese-Ragona et al. .......................... 356/602 |
| 6,164,894 | A | * | 12/2000 | Cheng ........................ 414/936 |
| 6,181,427 | B1 | * | 1/2001 | Yarussi et al. .............. 356/445 |
| 6,238,515 | B1 | * | 5/2001 | Tsujimoto et al. ........ 156/379.8 |
| 6,259,960 | B1 | * | 7/2001 | Inokuchi .................... 700/110 |
| 6,263,099 | B1 | * | 7/2001 | Maeda et al. ............... 382/149 |
| 6,310,985 | B1 | * | 10/2001 | White ........................ 382/289 |
| 6,320,609 | B1 | * | 11/2001 | Buchanan et al. .......... 348/126 |
| 6,338,971 | B1 | * | 1/2002 | Yasuda et al. ................. 438/14 |
| 6,363,168 | B1 | * | 3/2002 | Kakuma ..................... 382/151 |
| 6,414,752 | B1 | * | 7/2002 | Sullivan et al. .......... 356/237.5 |
| 6,477,266 | B1 | * | 11/2002 | Asar .......................... 382/147 |
| 2004/0046959 | A1 | * | 3/2004 | Meeks et al. ............... 356/369 |

FOREIGN PATENT DOCUMENTS

| | | |
|---|---|---|
| WO | WO92/04620 | 3/1992 |
| WO | WO96/27786 | 9/1996 |
| WO | WO97/17639 | 5/1997 |
| WO | WO99/15710 | 4/1999 |
| WO | WO 00/28577 | 5/2000 |

OTHER PUBLICATIONS

Nova Measuring Instruments Ltd. NovaScan 420 (Ophir Optronics Ltd.).

R. C. Gonzales and R.E. Woods, "Digital Image Processing", 1992, pp. 6-17.

Media Cybernetics, Image-Pro PlusTM (1993), 6 pages.

Matrox Electronic Systems, LTD., Matrox ITOOLS (Jan. 1993), pp. 1-5.

Matrox Genesis PCI Image Processor, "Technical Brief" (Oct. 1, 1996), pp. 1-15.

Matrox Electronic Systems, LTD, Matrox Genesis (Oct. 1, 1996), 6 pages.

Matrox Electronic Systems, LTD, Matrox Imaging Library (MIL) (Feb. 23, 1996) pp. 4.

Matrox Electronic Systems, LTD, Matrox Imaging Library Version 4.0 (Nov. 1, 1996), 7 pages.

PROMETRIX, FT-700TM, Film thickness Probe with Stat Trax® version 6.0, "User's Guide" (Jul. 1993), 11 pages.

\* cited by examiner

METROLOGY/INSPECTION POSITIONING SYSTEM

CROSS REFERENCE TO RELATED APPLICATION

This is a continuation-in-part of and incorporates by reference in its entirety, co-owned U.S. patent application Ser. No. 09/113,484, entitled "System using a Polar Coordinate Stage and Continuous Image Rotation to Compensate for Stage Rotation," filed Jul. 10, 1998, issued on Nov. 20, 2001 as U.S. Pat. No. 6,320,609 B1.

BACKGROUND

Field of the Invention

This invention relates to measurement and inspection systems and particularly to systems and methods for measuring or inspecting specific locations on a wafer while the wafer remains in a processing apparatus.

Description of Related Art

During fabrication of semiconductor devices, wafers containing devices are often inspected or measured to determine whether processes are proceeding as expected. Such measurements provide information that guides adjustments of process parameters to improve the yield of operable devices.

Typically, the inspection or measurement of a wafer requires moving the wafer to a metrology station where the wafer is mounted on a precision stage. The stage precisely positions the wafer to allow inspection or measurement of specific points on the wafer. Standalone metrology stations have drawbacks including: the space required for the station; the processing delay for removing, measuring, and returning the wafer for further processing; and possible contamination or damage to the wafer that moving the wafer introduces. Metrology equipment that measures or inspects a wafer while the wafer remains in a processing apparatus would avoid many of the drawbacks of standalone stations. However, the typical processing apparatus lacks a stage or other means capable of precisely positioning a wafer for inspection or moving in the wafer in response to the needs of the metrology equipment. Further, the space available in and around processing apparatuses is limited so that compact equipment is required.

Many measurement and inspection systems mount samples such as semiconductor wafers on X,Y stages. An X,Y stage can move a sample in two independent orthogonal directions X and Y to select an area of the sample for viewing, imaging, or measurement. For example, an X,Y stage can move a wafer to select and position an area of the wafer in the field of view of an imaging system. The travel distances of the X,Y stage in the X and Y directions determine the size of the largest sample that can be inspected from edge to edge, and large samples require large travel distances. Accordingly, inspection systems have become larger to accommodate larger samples, for example, larger diameter semiconductor wafers.

The space required to accommodate the range of motion of an X,Y stage has a width that is equal to or greater than the width of the sample plus the travel distance in the X direction and a length that is equal to or greater than the length of the sample plus the travel distance in the Y direction. FIG. 1 illustrates a system 100 that uses an X,Y stage to position a circular sample 110. System 100 includes an imaging and/or measurement system (not shown) that can be, for example, a video camera, a microscope, an interferometer, a reflectometer, an ellipsometer, an FTIR spectrometer, or any type of spectrophotometer. Such systems typically have a field of view 130 that is much smaller than sample 110. To view the left edge of sample 110, the X,Y stage moves sample 110 to a position 112 where the left edge of sample 110 is in field of view 130. Position 112 is offset to the right from the central position of sample 110 by the radius r of sample 110. A position 116 for viewing the right edge of sample 110 is offset a distance r to the left along the X axis from the central position. Accordingly, the X,Y stage must have a travel distance of 2r along the X axis for edge-to-edge inspection of sample 110. Similarly, the X,Y stage must have a travel distance of 2r along the Y axis between positions 114 and 118, and a minimum area 120 required for an X,Y stage capable of positioning sample 110 for edge-to-edge viewing is about $16*r^2$.

Many applications require the sample to be accurately positioned and oriented or at least require accurate information regarding the position and orientation of the sample relative to the X,Y stage. This requirement is common in automated semiconductor manufacturing where the samples are generally round semiconductor wafers. A wafer's position can be accurately determined by rotating the wafer about a rotation axis and monitoring the variation in the perimeter location of the wafer as a function of the rotation. An analysis of the measured perimeter variations can accurately determine the offset from the rotation axis to the center of the wafer. Additionally, the process can identify the orientation of the wafer because most semiconductor wafers have an orientation indicator such as a notch or a flat on its perimeter. An edge detector detects when the flat or notch in the wafer's perimeter rotates past. Examples of such position detector systems, which are often referred to as prealigners, are described in U.S. Pat. No. 4,457,664 of Judell et al., U.S. Pat. No. 5,308,222 of Bacchi et al., U.S. Pat. No. 5,511,934 of Bacchi et al., and U.S. Pat. No. 5,513,948 of Bacchi et al. Prealignment for an X,Y stage requires addition of structure such as a separate prealignment station, from which the wafer is transferred to the X,Y stage after prealignment, or a rotatable sub-stage on the X,Y stage for rotating the wafer.

FIG. 2 illustrates a system 200 using a polar coordinate stage 220 to position sample 110. Polar coordinate stage 220 has a rotatable platform mounted on a linear drive mechanism. The linear drive mechanism moves the platform and a sample along a coordinate axis R, and the platform rotates the sample about the rotation axis of the platform. Polar coordinate stage 220 requires significantly less area when positioning sample 110 for edge-to-edge inspection. In particular, a travel distance r (the radius of the sample) along axis R out to a position 212 is sufficient to center in field of view 130 any radial coordinate ρ in the range from 0 to r. Rotation of sample 110 then selects an angular coordinate θ so that any point on sample 110 can be positioned in field of view 130. Since polar coordinate stage 220 only requires one-dimensional linear motion and half the travel distance of an X,Y stage, the polar coordinate stage takes much less area than an X,Y stage requires. In particular, a polar coordinate stage needs an area of about $6*r^2$, which is less than 40% of the area that an X,Y stage requires.

A disadvantage of a polar stage is the portion of sample 100 in field of view 130 generally appears to rotate when the stage rotates sample 100 to move from one inspection location to another. Thus, different areas appear to have different orientations when an operator or machine vision software views the sample through an imaging system. Additionally, the speed of movement generally varies from one location to another for any constant stage rotation speed. In some measurement systems, an operator observes an image of a portion of the sample being measured or inspected and controls movement of the sample to select which areas are measured or inspected. With a polar stage, image rotation and variable image motion can easily confuse or disorient the operator when the operator is continuously viewing or inspecting sample 110 and moving the sample from one position to another. Accordingly, systems and methods are sought that provide the area savings of a polar coordinate stage but avoid the confusion of image rotation and variable speeds of motion.

SUMMARY

In accordance with an aspect of the invention, a metrology/inspection system moves the optics and/or measuring equipment above a wafer or sample being inspected or measured. Thus, the metrology or inspection system permits inspection or measurement of a wafer through a window in a processing apparatus. Positioning typically requires pre-alignment to at least roughly determine the location and orientation of the wafer relative to the apparatus, and alignment which precisely identifies the position and orientation of specific features on the wafer. In accordance with an aspect of the invention, the pre-alignment uses edge detection that avoids the inaccuracy arising from pattern recognition systems. With the orientation of the wafer identified, an image rotation system presents an image of the wafer with a standard orientation. The standard orientation facilitates identification of features on the wafer, inspection of the wafer, and operation of metrology equipment to move from point to point on the wafer. More specifically, the image rotation system can maintain the standard orientation of an image of the wafer as an operator moves the optics from one inspection area to the next.

In one specific embodiment of the invention, the apparatus includes an R-θ stage that positions optics relative to the wafer. A rotation axis of the R-θ stage can either be over or outside a view area of the system. The R-θ stage provides a compact means for positioning the optics while the image rotation and control system permit a user to control motion and view the wafer using perpendicular Cartesian axes and uniform velocity linear motion.

BRIEF DESCRIPTION OF THE DRAWINGS

Use of the same reference symbols in different figures indicates similar or identical items.

DETAILED DESCRIPTION

In accordance with an aspect of the invention, a system for measuring, viewing, or inspecting a sample uses a polar stage on which the sample is mounted. A control system which receives operator commands for linear movement of the sample, generates signals to the polar coordinate stage as reciuired to achieve the linear movement, and rotates the image during motion to preserve a fixed orientation of the sample as viewed by the operator. Accordingly, an operator can easily and intuitively control the direction and velocity of the sample's motion.

In accordance with another aspect of the invention, an edge detector detects the location of the edge of a circular sample such as a semiconductor wafer while the polar stage rotates the sample. Processing of the edge measurements allows a precise determination of the position of center of the wafer and identification of an orientation indicator such as a flat or a notch on the edge of the wafer. Accordingly, the stage does not require additional degrees of freedom or additional structures for prealignment of the wafer.

Figure 1:
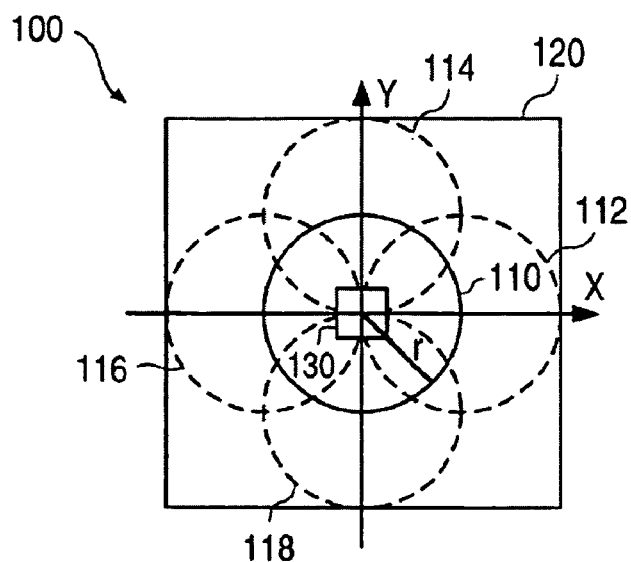
FIGS. 1 and 2 respectively illustrate the areas required for Cartesian and polar coordinate stages that have the same coverage capability.
Figure 2:
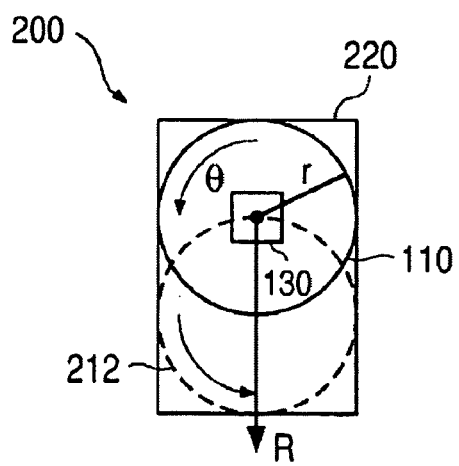
Figure 3:
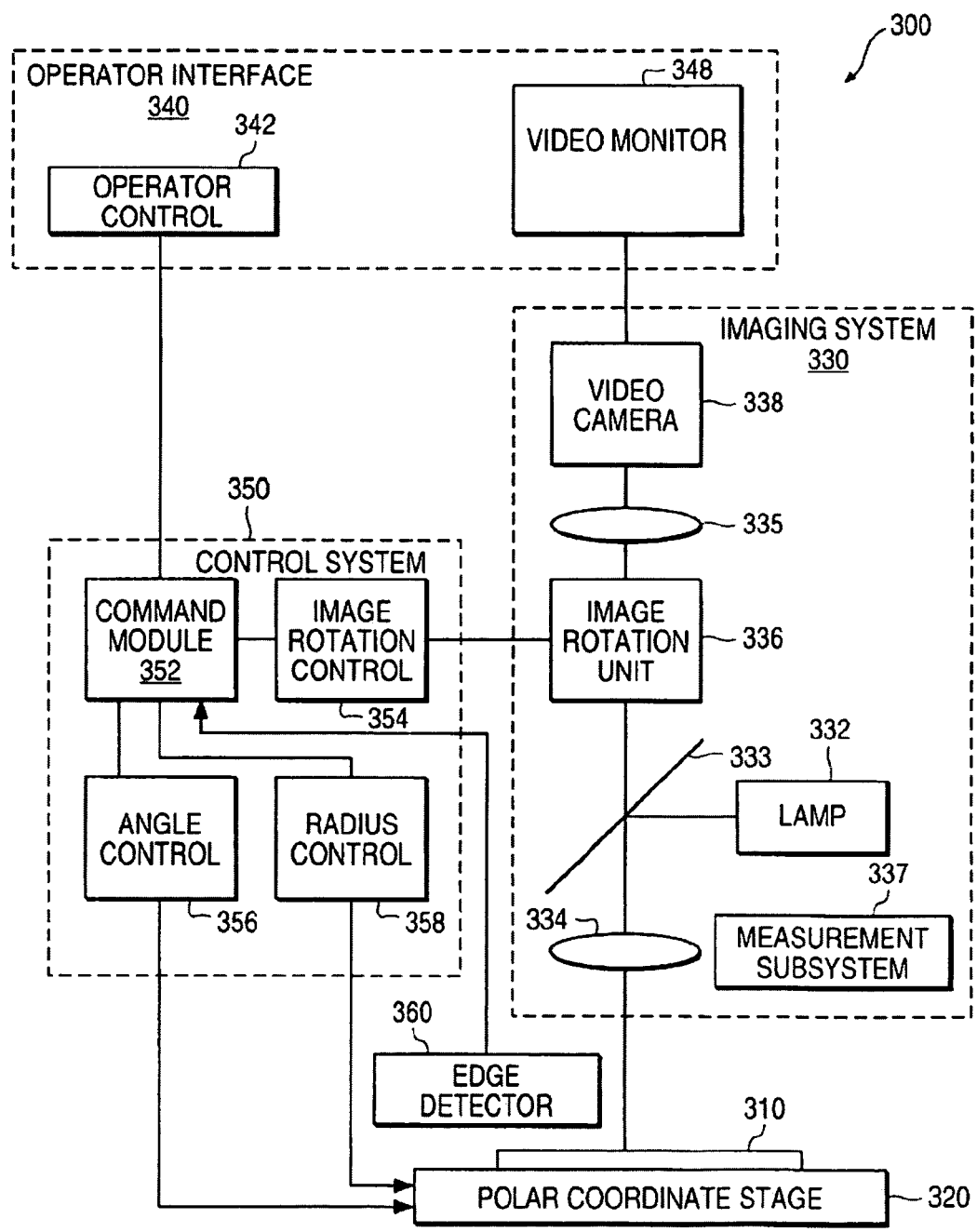
FIG. 3 is a block diagram of a embodiment of the invention using an optical microscope and optical image rotation.

FIG. 3 illustrates a measurement system 300 in accordance with an embodiment of the invention. System 300 includes a polar coordinate stage 320, an imaging system 330, an operator interface 340, a control system 350, and an edge detector 360. Polar coordinate stage 320 is a standard polar coordinate stage such as commercially available from a variety of sources and includes a linear drive that moves a rotatable platform on which sample 310 is mounted. Polar coordinate stage 320 can rotate sample 310 by 360° about a rotation axis of the platform. A rotary encoder monitors the angular orientation θ of the platform relative to a linear drive direction, which is the direction along which the linear drive moves the platform as the linear drive setting ρ changes. The linear drive direction is also referred to herein as the R coordinate axis. A linear encoder monitors the linear position of the platform along the R coordinate axis. The maximum linear travel of the platform along the R coordinate axis determines the radius of the largest sample which imaging system 330 can view completely, assuming that imaging system 330 is stationary.

Imaging system 330 is for viewing or inspecting regions of sample 310. In system 300, imaging system 300 is an optical microscope that includes a lamp 332. a beam splitter 333, lenses 334 and 335, and a camera 338. In operation, beam splitter 333 reflects light from lamp 332 onto an object area on sample 310, and objective lens 334 produces a magnified reflected light image of the object area. Lens 335 projects the image into camera 338, and camera 338 generates a signal representing the image that a monitor 348 displays. Lenses 334 and 335 are merely illustrative of optical elements. Additional optical elements are typically reciuired to achieve the desired field of view and magnification of a suitable imaging system 330. In one embodiment, imaging system 330 includes a confocal microscope.

A measurement subsystem 337 can also be associated with imaging system 330 to measure particular properties, such as reflectance, at a point in or near the region of sample 310 being viewed. For example, measurement subsystem 337 may include measuring equipment that measures reflectance at one or more points in the field of view. In an optical system, measurement subsystem 337 may include for example, an interferometer, a reflectometer. an ellipsometer, an FTIR spectrometer, or any type of spectrophotometer. Subsystem 337 can measure sample 310 through other elements of imaging system 330 or operate independently to measure a point or points in or near the field of view of imaging system 330.

Imaging system 330 further includes image rotation optics 336 which provide an adjustable rotation of the image to cancel image rotation that stage 320 causes when moving sample 310. In an exemplary embodiment of the invention, image rotation optics 336 includes a motor driven dove prism. Dove prisms are well known optical elements that provide image rotation about an optic axis, in this case the optical axis of imaging system 330. Control system 350 generates a signal that rotates the dove prism at a rate that compensates for rotation of sample 310 and prevents the image formed in camera 338 from rotating.

In an alternative embodiment, imaging system 330 includes a scanning beam microscope such as an electron beam microscope or an ion beam microscope that scans a region of sample 310 and forms a video image. The video image conventionally has horizontal raster lines which correspond to the scanning direction of the scanned beam. In such an embodiment, image rotation unit 336 includes a beam deflection system that can rotate the direction of scanning. Rotating the direction of scanning direction results in a rotation of the image on monitor 348.

Operator interface 340 is for observing the image of an object area of sample 310 and controlling movement of the field of view of imaging system 330 across sample 310. Operator interface 340 includes monitor 348 and operator control 342. Monitor 348 is a conventional video monitor capable of displaying an image represented by a signal from video camera 338. In particular, monitor 348 displays the image of the object area of sample 310. and an operator uses operator control 342 to change the object area in the field of view of imaging system 330. Operator control 342 is for inputting movement commands and directing the motion of the field of view across sample 310. In an exemplary embodiment of the invention, operator control 342 is a joystick but many alternative operator controls are suitable. For example, a region of monitor 348 can display control buttons that are software operated through the actions of a touch sensitive screen, a mouse, a track ball, a touch pad, or another pointing device. In the exemplary embodiment, an operator, observing the image from camera 338 on monitor 348, moves the joystick in a direction which corresponds to the direction in which the field of view should move relative to the displayed image. The degree of joystick movement determines the speed of image motion.

Control system 350 is a computer system that receives control signals from operator interface 340 and generates control signals to stage 320 and imaging system 330. Control system 350 includes a command module 352 that interprets the signals from operator control 342 and generates signals for controlling stage 320 and imaging system 330. In particular, command module 352 includes software that control system 350 executes to monitor and control ρ and θ settings of stage 320 and control the angle through which image rotation unit 336 rotates the image. As stage 320 moves sample 310, command module 352 sends a command via image rotation control unit 354 to image rotation unit 336 which responds by rotating the image. The image rotation is in a direction opposite the rotation of sample 310 so that the orientations of features appearing in the image remain fixed on monitor 348. For example, when the operator directs movement of the image along a feature that initially appears horizontal on monitor 348, control system 350 generates and applies a control signal to image rotation unit 336 to compensate for stage 320 rotating sample 310, and the feature in the image remains horizontal as the image moves. In the exemplary embodiment, image rotation control 354 includes a hardware interface conveying information to and from image rotation unit 336.

Control system 350 also determines and applies signals to an angle control unit 356 and a radius control unit 358 so that stage 320 moves sample 310 at the desired speed in the desired direction relative to the displayed image. In the exemplary embodiment, control units 356 and 358 combined include a hardware interface conveying information to and from stage 320. Known computer controlled polar stages and their interfaces are suitable for system 300. Control system 350 further receives signals from edge detector 360 for a prealignment process described below. The prealignment process provides a precise indication of the orientation and position of sample 310.

Figure 4:
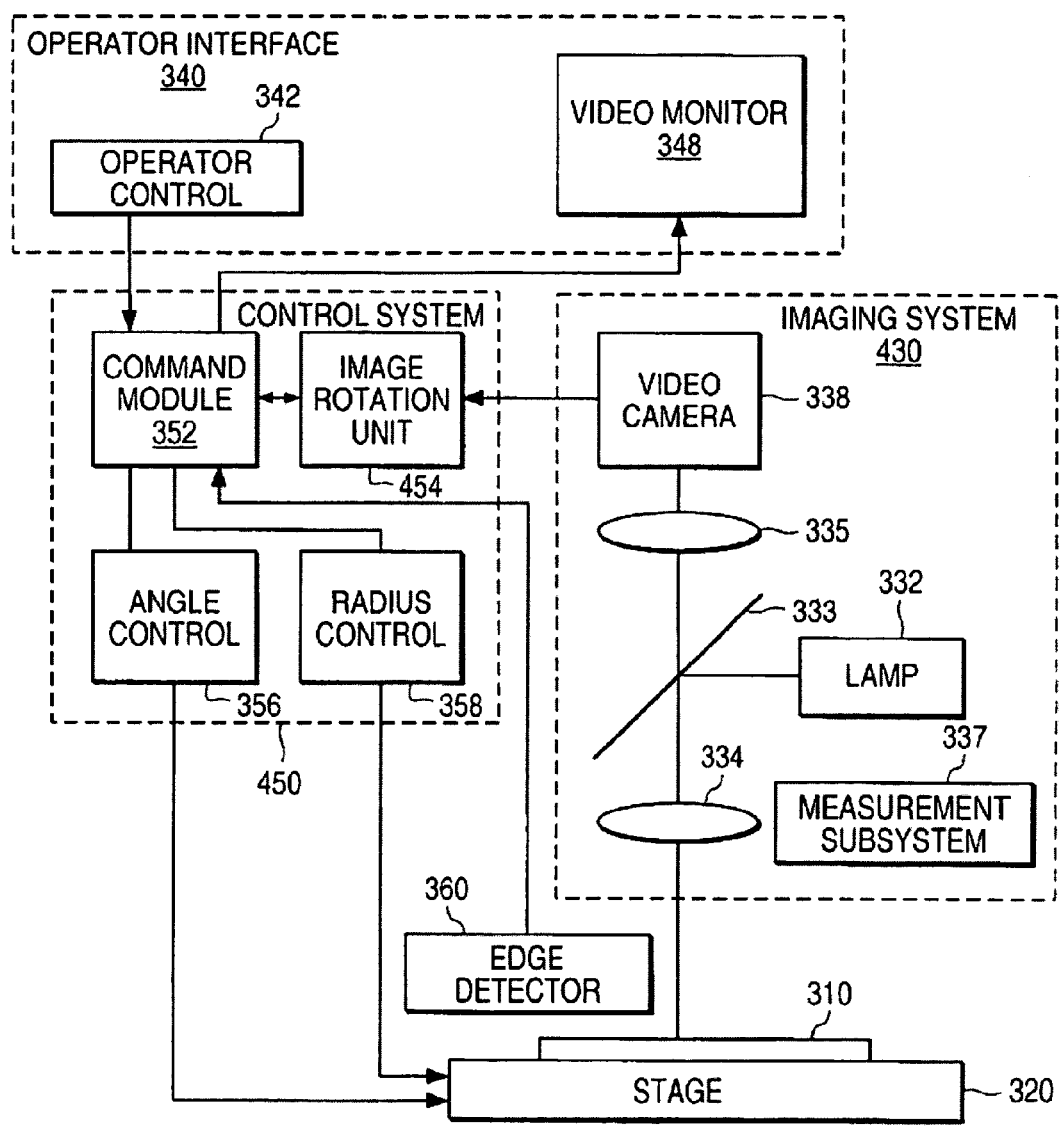
FIG. 4 is a block diagram of an embodiment of the invention using software to rotate an image.

FIG. 4 is block diagram of an inspection or measurement system 400 that uses software for image rotation. System 400 includes a stage 320, an operator interface 340, an edge detector 360, and a measurement subsystem 337 which are the same as those described above in regard to system 300 of FIG. 3. System 400 also includes an imaging system 430 and a control system 450. In system 400, imaging system 430 does not include an optical or mechanical system for rotating the image. Instead, control system 450 includes an image rotation unit 454. Image rotation unit 454 includes an acciuisition board that receives a video image signal from camera 338 and a module from rotating the video image. Typically, software performs the image rotation, but alternatively, hardware could be designed that electronically rotates the image. When command module 352 directs stage 320 to rotate sample 310, the image from camera 338 is of a rotating (and moving) portion of sample 310. Image rotation unit 454 processes the input video signal to compensate for the rotation and generates an output video signal representing a moving image which preserves the orientations of features on sample 310. Control system 450 then provides a video signal representing the corrected image to video monitor 348.

In one exemplary embodiment of system 400, stage 320 is a polar stage available from Kensington Laboratories and is used to mount semiconductor wafers up to 200 mm in diameter. Additionally, a z coordinate stage can be added to or integrated into stage 320 for focusing for imaging system 430 and/or measurement system 337. For example, imaging system 330 can attach to the z coordinate stage for focusing on a wafer on the polar coordinate stage. Imaging system 430 includes an optical microscope that provides a field of view at sample 310 which is about 1.3 mm×1 mm. Imaging system 430 also directs light from a small spot (about 15 microns in diameter) at the center of the field of view to a spectrometer which collects data on the reflectance. This data can be used for determining the film thickness. A co-filed provisional U.S. patent application, entitled "Compact Optical Reflectometer System", of R. Yarussi and Blaine R. Spady, Ser. No. 60/092,384, describes some suitable measuring and imaging systems and is hereby incorporated by reference in its entirety.

Control system 450 is a computer such as a 400 MHz Pentium Il-based personal computer having a video capture board for connection to video camera 338 and an interface for connection to stage 320. Video capture boards capable of performing real time image rotation are commercially available from a variety of sources including, for example, Visicom, Inc. The interface board required for connecting control system 450 to stage 320 depends on the stage manufacturer. In this embodiment, operator control 342 is implemented in software as controls appearing on monitor 348.

Before an operator uses system 300 or 400 to measure or inspect sample 310, prealignment and alignment processes accurately determine the position and orientation of sample 310. Typically when a sample such as a wafer is placed onto stage 320, the position of the center of sample 310 is known only to within one or two millimeters, and the angular orientation of the sample 310 may be completely unknown. In accordance with an aspect of the invention, a prealignment procedure uses edge detector 360 and stage 320 to determine the position and orientation of sample 310. For the prealignment procedure, a light source (not shown) below sample 310 illuminates sample 310, and sample 310 casts a shadow onto edge detector 360. Edge detector 360 includes a linear detector array located above sample 310 and precisely identifies the edge location of the shadow of sample 310 while stage 320 rotates sample 310 through 360°. If sample 310 is nearly circular but not perfectly centered on the stage, the position of the shadow on detector 360 moves slightly as stage 320 rotates sample 310.

Figure 5:
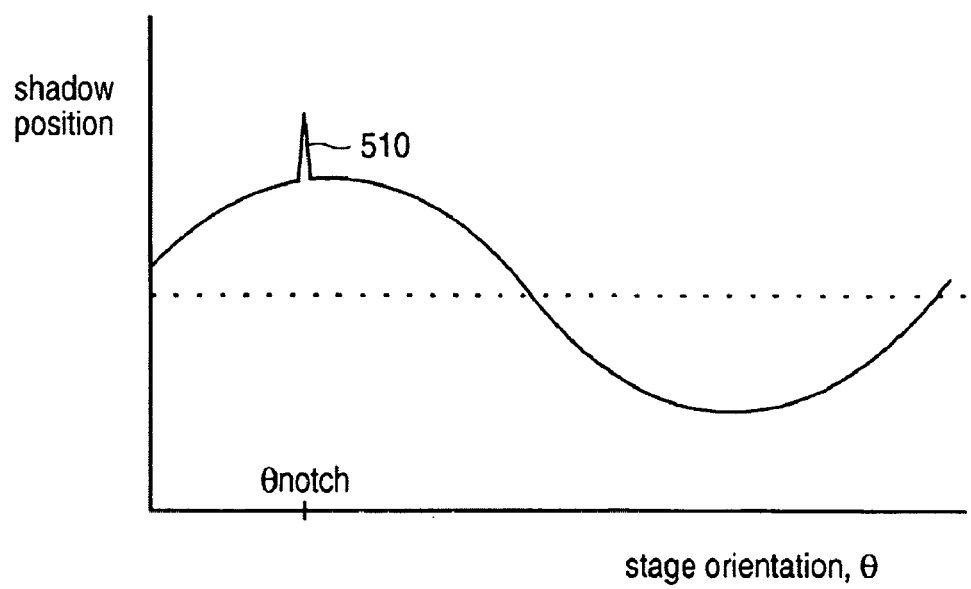
FIG. 5 is a plot of edge position measurements used in a prealignment process for the system of FIG. 3 or 4.

FIG. 5 shows a typical graph of the angular position of stage 320 versus the position of the shadow of sample 310 when sample 310 is a circular wafer having a notch in its perimeter. The position of the shadow of sample 310 generally follows a sinusoidal curve except where the notch causes a spike 510 in the sinusoid. The angular orientation of sample 310 is found from the position of spike 510. The offset of the center of sample 310 from the rotation axis of stage 320 is a vector having a direction identified from maxima/minima of the sinusoidal curve and a magnitude of half the amplitude of the sinusoidal curve. Known statistical analysis techniques can be applied to the shadow position measurements (neglecting the spike) to determine the offset. For the exemplary embodiment of system 400, the position of the wafer is then found within approximately 0.2 mm.

This is not accurate enough for many applications. The next level of alignment is a deskew procedure. This procedure can be done with a video camera that looks at a field of view on the order of 1 mm×1 mm and identifies a feature such as an alignment mark in the field of view of sample 310. Imaging systems 330 (FIG. 3) and 430 (FIG. 4) fit these requirements, and can be used for the alignment process. Since the prealignment procedure aligns sample 310 to approximately 0.2 mm, a 1 mm×1 mm field of view centered on the expected location of the desired feature will include the feature. Pattern recognition software executed in the control system can then be used to find the position of the feature to within a few microns. Repeating the alignment process with a feature in another location on sample 310 can accurately find the position and orientation of sample 310. If stage 320 is accurate enough, any point on sample 310 can be found within a few microns simply by controlling the settings of stage 320. If stage 320 is not sufficiently accurate, the pattern recognition is repeated at subsequent measurement points. Now that the wafer has been accurately located, optical measurements can be made.

Figure 6:
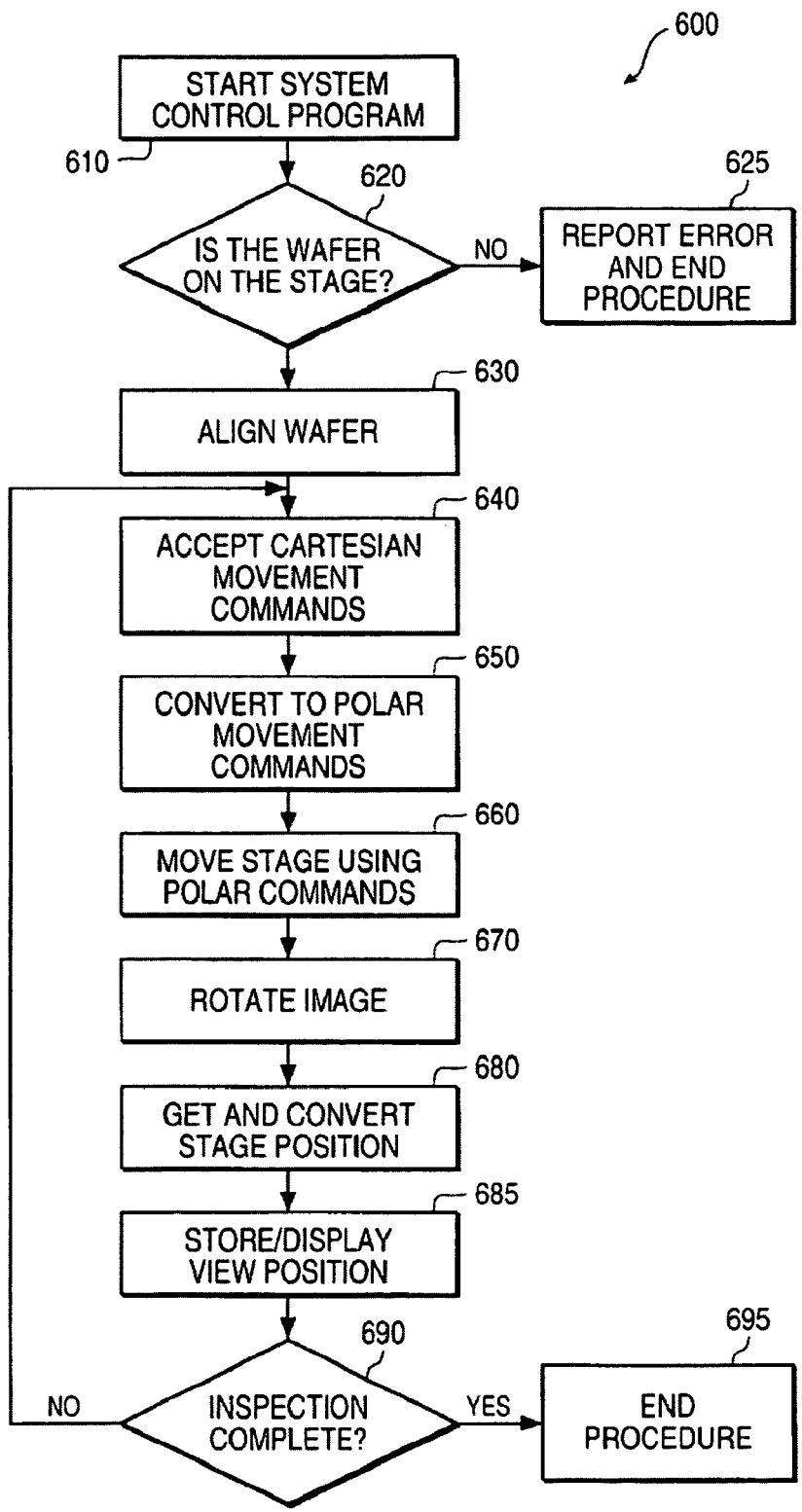
FIG. 6 is a is a flow diagram of a system control program for the system of FIG. 3 or 4.

FIG. 6 shows a flow diagram illustrating a process 600 for control of the polar coordinate stage 320 and image rotation unit 454 and determination of the position of sample 310 on stage 320 of FIG. 4. during measurement or inspection of sample 310. An initial block 610 initiates the system control program in control system 450. An initial inciuiry 620 of process 600 determines whether sample 310 is present on stage 320. An object-present sensor or the operator responds to inquiry 620. If no sample is present, process 600 ends in step 625 by reporting an error (no sample present). If sample 310 is present, block 630 implements the prealignment/alignment process described above. In particular, stage 320 rotates sample 310, edge detector 360 measures edge positions, and control system 450 analyzes the edge position measurements to identify an offset between the rotation axis of stage 320 and the center of sample 310. If necessary, sample 310 is then more precisely aligned or located using a deskewing procedure. Prealignment/alignment step 630 can be omitted when precise alignment of sample 310 is not required, for example, when sample 310 is simply inspected visually.

Once sample 310 is present and properly aligned, process 600 moves sample 310 according to the commands from an operator. In step 640, control system 400 receives Cartesian input commands from the operator. The input commands indicate a desired movement direction and speed relative to the image on monitor 348. Step 650 converts the Cartesian input commands to polar coordinate output commands for stage 320, and block 660 applies the appropriate signals to stage 320 to move sample 310. Step 670 is simultaneous with step 660 and rotates the image to cancel the rotation of sample 310 in step 660.

Figure 7:
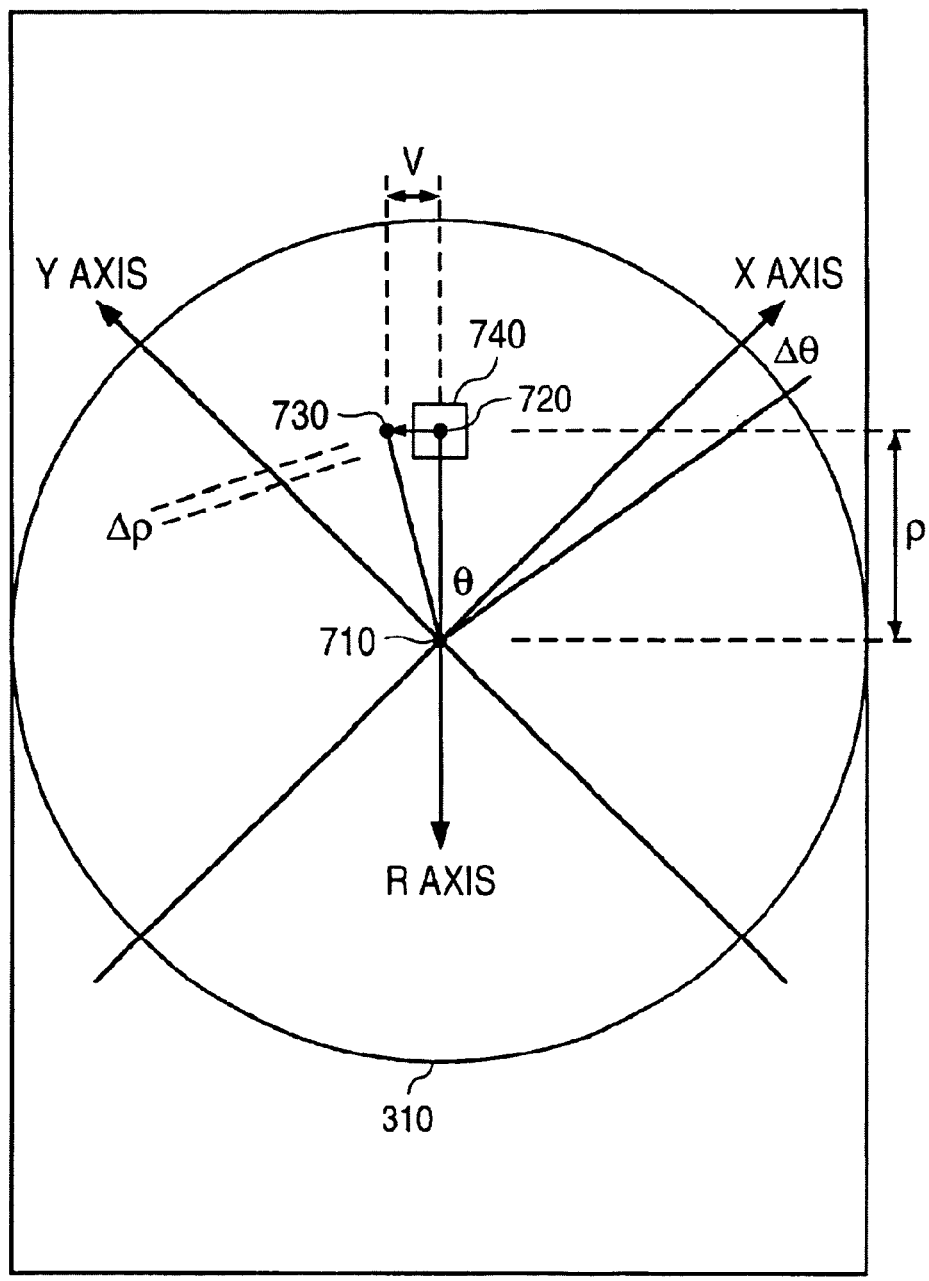
FIG. 7 illustrates the relationship between the image axes and stage axes.

To illustrate conversion and image rotation steps 660 and 670, FIG. 7 shows the relationship between the X and Y coordinate axes and the R coordinate axis of stage 320. The and Y axes are fixed on sample 310 and centered on the rotation axis 710 of the platform on which sample 310 is mounted. As noted above, rotation axis 710 is typically offset from the center of sample 310 by an amount determined during prealignment and/or alignment. Rotation axis 710 of stage 320 passes through the R coordinate axis. The R coordinate axis corresponds to the direction of linear motion of stage 320 and has an origin that remains in the center of a field of view 740 of the imaging system. A view point 720 on sample 310, which is currently at the center of field of view 740, has polar coordinates ρ and θ relative to rotation axis 710. Coordinate ρ is the distance that stage 320 moved sample 310. Coordinate θ is the angle through which stage 320 rotated sample 310.

Image rotation 670 preserves the orientation of the X and Y axes as viewed on monitor 348. For example, the X axis if initially horizontal remains horizontal on monitor 348 regardless of how stage 320 rotates sample 310. Accordingly. if the X axis is initially along the R axis, step 670 rotates the image by -θ, where θ is the polar coordinate of view point 720.

In general, the Cartesian input commands indicate a vector V having X and Y components Vx and Vy, and the magnitude |V| of the vector indicates the speed of movement of the view point in the image. In one embodiment of the invention, step 650 continuously converts velocity components Vx and Vy to a radial velocity Vr and an angular velocity ω. Radial velocity Vr controls the velocity at which stage 320 moves sample 310 in along the R axis, and angular velocity ω determines the angular velocity of rotation of sample 310. The velocity components can be determined from vector V and the coordinates of view point 720 using equations 1.

$$Vr = Vx*\cos\theta + Vy*\sin\theta$$

$$\omega = (Vx*\sin\theta - Vy*\cos\theta s\theta)  \quad\quad \text{Equations 1}$$

Alternatively, when stage 320 uses coordinate settings rather than velocity settings, the input commands are sampled at a fixed frequency so that the components Vx and Vy indicate small displacements ΔX and ΔY which are the product of the velocity components and the time between samples. Displacements ΔX and ΔY shift a point 730 to the center of the field of view 740. In this case, step 650 converts the displacements ΔX and ΔY to polar displacements Δθ and Δρ. The polar displacements Δθ and Δρ have magnitudes that depend on displacements ΔX and ΔY and the coordinates (X,Y) or (θρ) of current view point 720. Such conversions involve well known geometric techniques. It is desirable that stage 320 move sample 310 uniformly so that the displacements ΔX and ΔY require the full time between consecutive samplings of the input commands. Accordingly, to achieve this, the stage velocities need to vary according to the magnitude |V|, and the angular velocity needs to vary with radius. However, discontinuous shifts of sample 310 are imperceptible by the operator if the sampling period is sufficiently short, for example, if the sampling and shifting rate is higher than the frame rate of monitor 348.

A step 680 gets and converts the stage position, and a step 685 can then store or display the position and the rotated image for inspection process 600. After display of the inspection point, step 690 determines whether the inspection is complete. If not, process 600 branches back to step 640 to accept further Cartesian movement commands for movement to another inspection point. If the inspection is complete, process 600 ends in step 695.

In accordance with an aspect of the invention, a metrology/inspection system moves the optics and/or measuring equipment of the system relative to a wafer. Accordingly, measurement or inspection of the wafer does not require that the wafer be mounted on a precision stage. This allows the wafer to be at rest on any stationary structure, for example, in a processing apparatus when the system measures or inspects the wafer. In one embodiment, the metrology/inspection system examines a wafer through an optical window while the wafer sits at a cool-down station of a processing apparatus. Accordingly, measurement does not require removing the wafer from the processing apparatus and does not delay processing since the wafer can be measured, for example, during a required cool down period in device fabrication process.

Figure 8:
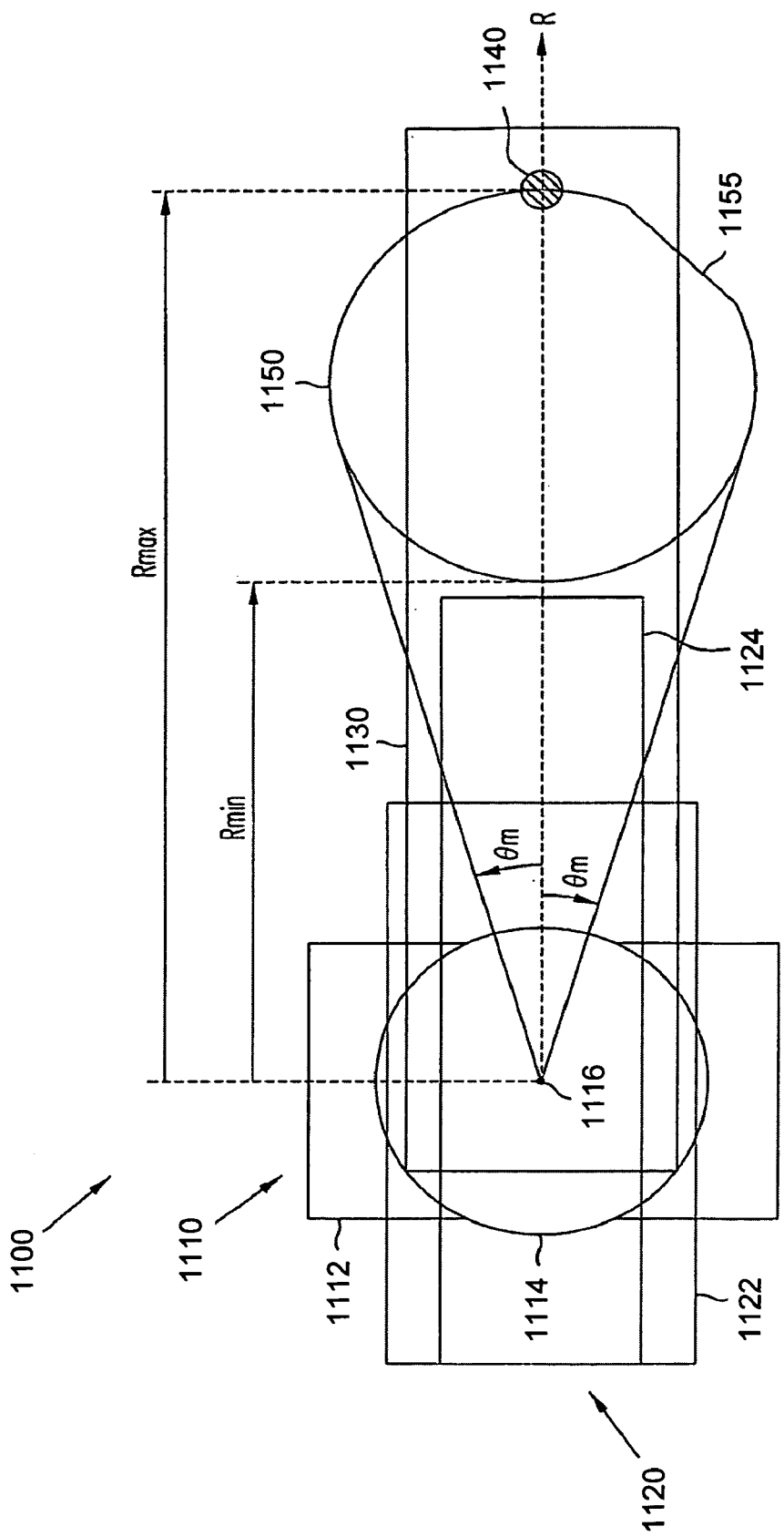
FIG. 8 shows a transparent top view of a metrology/inspection system in accordance with an embodiment of the invention.

FIG. 8 shows a top view of a metrology/inspection system 1100 in accordance with an embodiment of the invention. System 1100 includes a rotary stage 1110 having a base 1112 and a rotary portion 1114, a linear stage 1120 having a base 1122 and a slide portion 1124. Base 1122 of linear stage 1120 is mounted on rotary portion 1114 of rotary stage 1110. A case 1130, which contains measuring devices and an imaging system including an objective 1140, is mounted on slide portion 1124 of linear stage 1120. The combined movement of stages 1110 and 1120 can move objective 1140 radially towards and away from a rotation axis 1116 and rotate objective 1140 about axis 1116. Rotary and linear stages 1110 and 1120 position objective 1140 over a wafer for measurement or inspection of specific areas or features on the wafer. Rotary and linear stages with suitable precision are currently available from a variety of commercial sources and are commonly used to position wafers for processing. Commercially available R-θ stages can also accomplish the described movement of objective 1140.

The location of objective 1140, which is, for example, an objective lens of an optical system, establishes a measurement point or inspection area for the imaging system and measurement devices in case 1130. Movement of slide portion 1124 moves objective 1140 along a linear axis R. The range of motion of linear stage includes a minimum radius Rmin and a maximum radius Rmax, where the difference between Rmax and Rmin is greater than the diameter of a wafer or other sample 1150 by more than the expected error in the placement of sample 1150 for viewing. Rotation of rotary portion 1114 swings objective 1140 along an arc and changes the orientation of axis R of linear stage 1120. The angular range of motion of rotary stage 1110 is greater than twice the largest angle θm that a radius of sample 1150 spans relative to a rotation axis 1116 of rotary stage 1110. Larger ranges of motion permit positioning of system 1100 so that case 1130 does not block the view of sample 1150. Generally, polar coordinates r and θ associated with the orientations of stages 1110 and 1120 identify the location of objective 1140.

In an exemplary embodiment of the invention, objective 1140 is the objective lens of a reflected-light microscope. Typically, a video camera records the image from the microscope for image processing and/or display on a monitor (not shown). An operator of system 1100 uses the displayed image when inspecting the wafer or controlling movement for measurements at selected points on sample 1150. Measurement devices can tap and analyze part of the light from an optical imaging system including objective 1140, or the measurement devices can use their own sensors or optics. For example, a mirror in the optical path from objective 1140 can direct light to a spectrometer. The spectrometer measures the spectrum of light reflect from the wafer to identify constructive or destructive interference and identify the thickness of films on sample 1150. Further, the optical system may include other devices such as an OCR system or a bar-code reader that can read markings on sample 1150.

As described further below, an optical or electronic image rotation system rotates the image from the imaging system as required to present an image of a portion of sample 1150, with a standard orientation. One standard orientation, for example, has a flat 1155 on sample 1150 toward the bottom of the image, but any orientation of sample 1150 can be picked as the standard orientation. Having a standard orientation simplifies identification of particular points or areas on the wafer for viewing by objective 1140.

Figure 9:
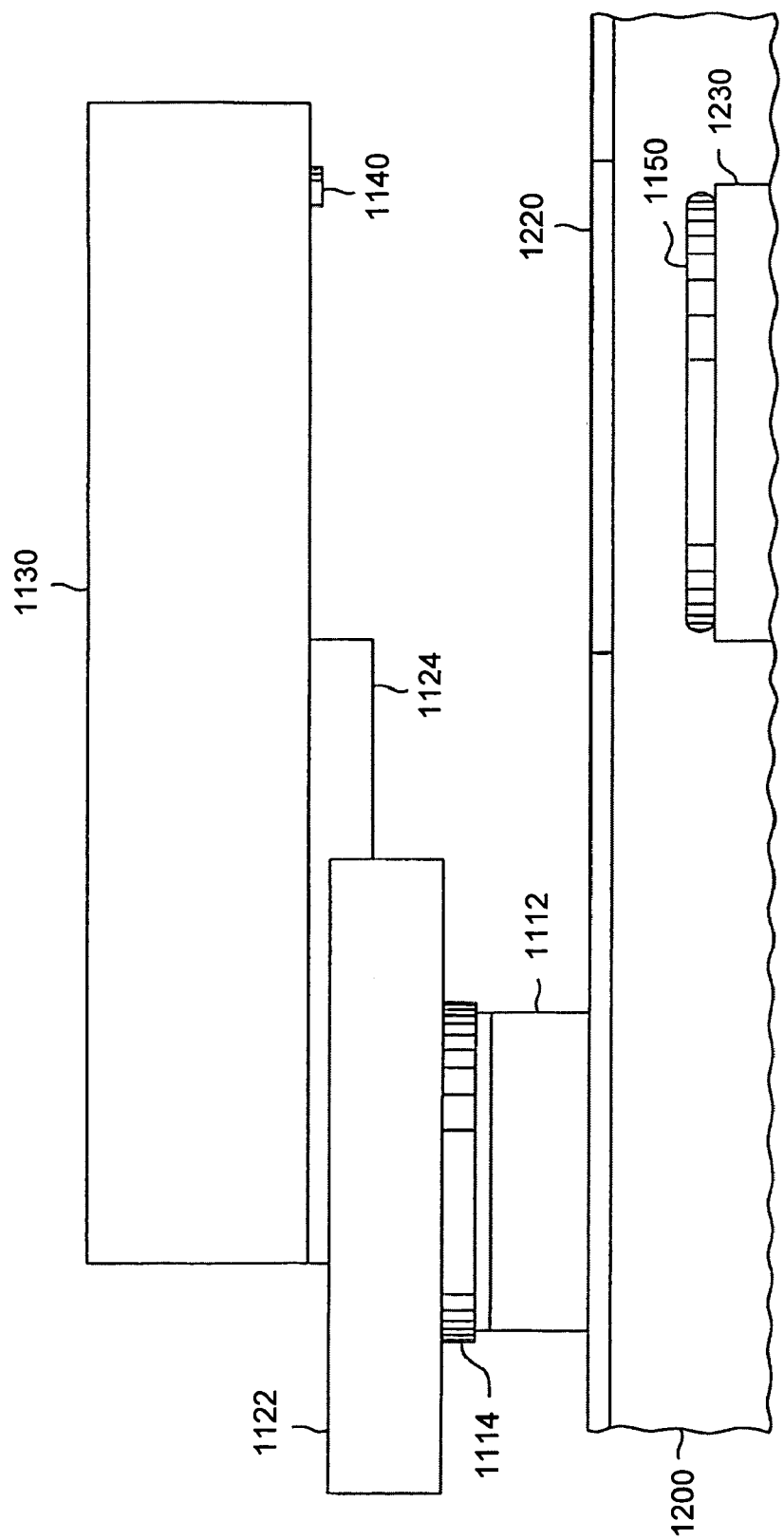
FIG. 9 shows side view of the system of FIG. 8 when mounted on an apparatus for processing wafers.

FIG. 9 shows a side view of the system 1100 when base 1112 of rotary stage 1110 is mounted on a processing apparatus 1200. Processing apparatus 1200 may for example be a CVD (chemical vapor deposition) chamber or PVD (physical vapor deposition) chamber. Apparatus 1200 includes a station 1230 such as a cool down station where sample 1150 rests. An optical window 1220 is located above station 1230 or otherwise position to permit viewing of sample 1150 through optical window 1220. Generally, processing equipment includes view window which can be replaced with optical grade window for use with measurement systems in accordance with embodiments of the present invention.

In one exemplary embodiment of system 1100, stages 1110 and 1120 are portions of a polar stage from Kensington Laboratories. The stage moves objective 1140 in a range between +105 mm to −105 mm from rotation axis 1116, and the angular movement of objective 140 up to 180 degrees. This permits inspection of wafers up to 200 mm in diameter. A great variety of other stages can be used for viewing of samples of various sizes. Additionally, a z coordinate stage can be added to or integrated into stages 1110 and 1120 for focusing of the imaging system. For example, case 1130 which encloses at least portions of the imaging system can attach to the z coordinate stage for focusing on sample 1150.

Figure 10:
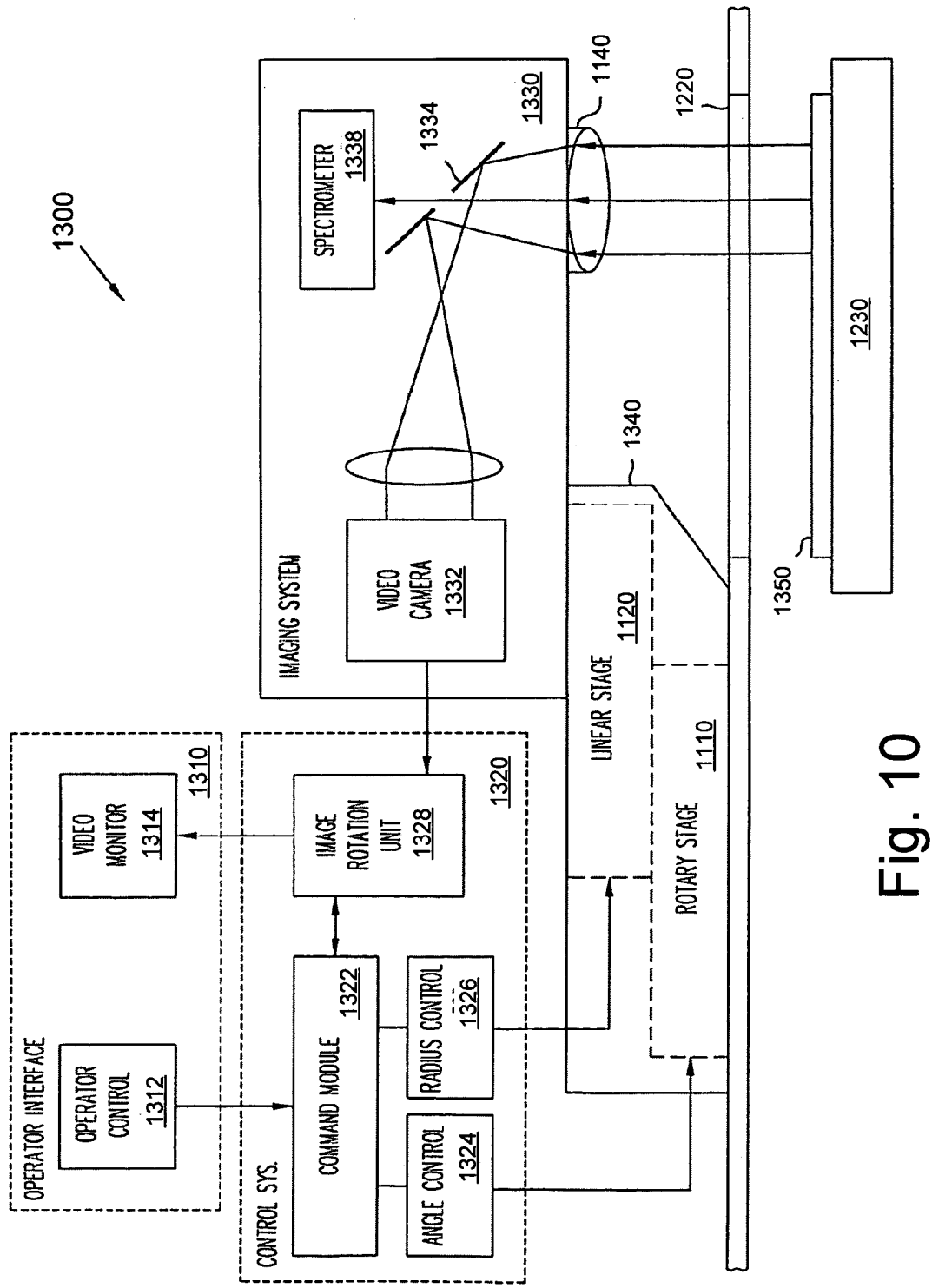
FIG. 10 is a block diagram of a metrology/inspection system in accordance with another embodiment of the invention.

FIG. 10 illustrates a metrology/inspection system 1300 in accordance with another embodiment of the invention. System 1300 includes an operator interface 1310, a control system 1320, an imaging system 1330, and a polar coordinate stage 1340. Polar coordinate stage 1340 can be a standard polar coordinate stage such as commercially available from a variety of sources. Alternatively, polar coordinate stage 1340 is a combination of rotary and linear stages such as described above. Polar coordinate stage 1340 changes the view point of the objective 1140 of imaging system 1330 by rotating imaging system 1330 about a rotation axis or by linear movement that changes a radial distance r from the rotation axis of stage 1340 to objective 1140. A rotary encoder monitors the angular orientation θ of the radial axis relative to a reference direction. The radial axis is along the linear drive direction and is also referred to herein as the R coordinate axis. A linear encoder monitors the linear position of objective 1140 along the R coordinate axis.

Operator interface 1310 and control system 1320 can be implemented in a computer system that includes appropriate hardware and software for the tasks described herein. For example, operator interface 1310 includes a video monitor 1314 that displays an image of an inspection area on a wafer 1350 and an operator control 1312 that allows the operator to select the inspected area.

Imaging system 1330 is for inspecting regions of wafer 1350. In system 1300, imaging system 1330 includes a visible or UV reflected-light microscope, a video camera 1332, an apertured mirror 1334, and a spectrometer 1338. In operation, a light source (not shown) illuminates a portion of wafer 1350, and some light reflected from wafer 1350 enters objective 1140. Mirror 1334 reflects a portion of the light from objective 1140 to video camera 1332 and passes a portion of the light from objective 1140 to spectrometer 1338. Camera 1332 generates a signal representing the image that a monitor 1314 displays. Objective lens 1140, mirror 1334, and camera 1332 are merely illustrative of typical optical elements. Generally, additional optical elements are required to achieve the desired field of view and magnification of a suitable imaging system 1330. In one embodiment, imaging system 1330 includes a confocal microscope.

Spectrometer 1338 is an example of a measurement subsystem associated with imaging system 1330 for measurement of particular properties at points on wafer 1350. Spectrometer 1338 measures the spectrum of the light reflected from wafer 1350 and from the relative reflectance of different wavelengths, can identify wavelengths particularly subject to constructive or destructive interference upon reflection from wafer 1350. Control system 1320 can identify film thicknesses from the spectrum that spectrometer 1338 measures. Imaging system 1330 can additionally or alternatively include other measurement subsystems such as an interferometer, a reflectometer, an ellipsometer, an FTIR spectrometer, or any other type of spectrophotometer. Spectrometer 1338 and other measurement subsystems can measure wafer 1350 through other elements (e.g., objective 1140) of imaging system 1330 or operate independently to measure a point or points in or near the field of view of imaging system 1330.

Video camera 1332 forms an image of a region of wafer 1350 and sends a signal representing the image to control system 1320. The orientation of the image depends on the orientation of wafer 1350 and the orientation of imaging system 1330. Accordingly, if the images from video camera 1332 were directly displayed on monitor 1314, matching areas of different wafers 1350 would be displayed with random orientations that depend on the orientations of the wafers. Such variations in the orientations of images would make the task of inspecting wafers more difficult. Further, when moving from one inspection area to another on wafer 1350, the images would rotate as imaging system 1330 rotates. Such image rotations make operator control of movement difficult. To avoid these problems, control system 1320 includes an electronic image rotation unit 1328 that rotates the image from video camera 1332 by an angle selected according to the orientations of wafer 1350 and imaging system 1330.

Optionally, imaging system 1330 may include active image rotation optics that provide an adjustable rotation of the image to cancel image rotation that stage 1340 causes when moving optical system 1330 or to correct for variation in the orientations of wafers 1350 being examined. In an exemplary embodiment of the invention, image rotation optics includes, for example, a motor driven dove prism. Dove prisms are well known optical elements that provide image rotation about an optic axis, in this case the optical axis of imaging system 1330. In an embodiment including active image rotation optics, control system 1320 generates a signal that controls the optical image rotation. For example, the optical system can rotate the image at a rate that compensates for rotation or movement of imaging system 1330.

In an exemplary embodiment, imaging system 1330 includes an optical microscope that provides a field of view at wafer 1350 which is about 1.3 mm × 1 mm. An aperture in mirror 1334 passes light from a small spot (about 15 microns in diameter) at the center of the field of view of objective 1140 to spectrometer 1338 which collects data on the reflectance. This data can be used for determining the film thickness. U.S. patent application entitled "Compact Optical Reflectometer System," of R. Yarussi and Blaine R. Spady, Ser. No. 09/347,362, issued on Jan. 30, 2001 as U.S. Pat. No. 6,181,427 B1, describes some suitable measuring and imaging systems and is hereby incorporated by reference in its entirety.

As mentioned above, operator interface 1310 enables observation of an inspection area of wafer 1350 and selection of the inspection area. Operator interface 1310 includes monitor 1314 and operator control 1312. Monitor 1314 is a conventional video monitor capable of displaying an image represented by a signal from video camera 1332. In particular, monitor 1314 displays the image of the inspection area of wafer 1350, and an operator uses operator control 1312 to change the inspection area. Specifically, operator control 1312 is for input of movement commands and directing the motion of objective 1140. In an exemplary embodiment of the invention, operator control 1312 is a mouse or keyboard that inputs commands to software in control system 1320. Alternatively, operator control 1312 can be a joystick, a touch sensitive screen, a track ball, a touch pad, or another pointing device. In the exemplary embodiment, an operator, observing the image from camera 1332 on monitor 1314, can use operator control 1312 to select the direction and speed of linear motion of the field of view relative to the displayed image. The operator can also select automatic movement to preselected areas on wafer 1350 or movement that follows features appearing in the image displayed on monitor 1314.

Operators observing image motion on monitor 1314 typically expect linear motion. Accordingly, control system 1320 generates commands to polar coordinate stage 1340 that cause linear motion of objective 1140 relative to wafer 1350. Additionally, to maintain the orientation of the displayed image, control system 1320 changes the amount that image rotation unit 1328 rotates the image from camera 1332.

In an exemplary embodiment, control system 1320 is a computer such as a 600 MHz Pentium II-based personal computer having a video capture board for connection to video camera 1332 and interfaces 1324 and 1326 for connection to stage 1340. Video capture boards capable of performing real time image rotation required of image rotation unit 1328 are commercially available from a variety of sources. The interface board required for connecting to stage 1340 depends on the type and manufacturer of stage 1340.

In control system 1320, a software command module 1322 interprets the signals from operator control 1312 and directs hardware control units 1324 and 326 to generate signals for controlling stage 1340 and image rotation unit 1328. In particular, command module 1322 includes software that control system 1320 executes to monitor and control r and θ coordinates of stage 1340 and control the angle through which image rotation unit 1328 rotates the image. Control system 1320 thus determines and applies signals to an angle control unit 1324 and a radius control unit 1326 so that stage 1340 moves imaging system 1330 at the desired speed in the desired direction. In the exemplary embodiment, control units 1324 and 1326 combined include a hardware interface conveying information to and from stage 1340. Known computer controlled polar stages and their interfaces are suitable for system 1300.

As stage 1340 moves imaging system 1330, command module 1322 commands image rotation unit 1354 to rotate the image. The image rotation has the same direction and rate as the rotation of imaging system 1330 so that the orientations of features appearing in the image remain fixed on monitor 1314. For example, when the operator directs movement of the image along a feature that initially appears horizontal on monitor 1314, control system 1320 generates and applies a control signal to image rotation unit 1328 to compensate for stage 1340 rotating imaging system 1330, and the feature in the image remains horizontal as the image moves.

In an exemplary embodiment of the invention, image rotation unit 1328 includes an acquisition board that receives a video image signal from camera 1332 and a module from rotating the video image. In the exemplary, embodiment the video image rotating module is a VigraVision PCI card from Visacomm, Inc., but alternatively, the module can be implemented in software. When command module 1322 directs stage 1340 to rotate wafer 1350, the image from camera 1332 is of a rotating (and moving) portion of wafer 1350. Image rotation unit 1328 processes the input video signal to compensate for the rotation and generates an output video signal representing a moving image which preserves the orientations of features on wafer 1350. Control system 1320 then provides a video signal representing the corrected image to video monitor 1314.

Before an operator uses system 1300 to measure or inspect wafer 1350, command module 1322 directs pre-alignment and alignment processes to accurately determine the position and orientation of wafer 1350. Typically, a sample such as a wafer placed at a station in a processing apparatus has a position that is known to an accuracy of one to several millimeters, and angular orientation of the wafer may be completely random or unknown. In accordance with an aspect of the invention, a pre-alignment procedure determines the position and orientation of wafer 1350 by detecting the edge and an alignment feature (e.g., a notch or flat) on the edge of wafer 1350.

For pre-alignment of a wafer 1350, command module 1322 directs stage 1340 to move objective 1140 until an edge of wafer 1350 is detected. An edge can be identified using video camera 1332 or using spectrometer 1338. Edge detection using video camera 1332 employs image recognition software that identifies an edge from contrast in the image. Spectrometer 1338 detects the edge as a drop in the measured reflectance for most or all wavelength as objective 1140 passes an edge of wafer 1350. Other resources in the optical system such as a reflectometer or other device that measures the intensity of reflected light could similarly detect the edge from a drop in reflected light. Alternatively, the pre-alignment process can use a separate edge detection system. Detecting three or four points on the edge of wafer 1350 is sufficient for identification of the position of wafer. Using edge detection and particularly using spectrometer 1338 avoids the difficulties the conventional image recognition software has when attempting to identify a structure on a wafer having a completely unknown alignment. After identifying a point on the edge of wafer 1350, command module 1322 then directs stage 1340 to move objective 1140 along the edge of wafer 1350 for detection of an alignment feature such as a notch or flat that indicates the orientation of wafer 1350. Once the notch or flat is found, the position and orientation of the wafer are known. However, the pre-alignment determination of position and orientation may not be sufficient for many applications. In particular, inspection and measurements of a wafer are typically of features formed on the wafer, and such features may not have a completely consistent position relative to the edge of wafer 1350.

The next level of alignment is a deskew procedure. The deskew procedure can be done with video camera 1332 and an image recognition module that identifies a feature such as an alignment mark in the field of view of video camera 1332. In particular, if the pre-alignment procedure aligns features on wafer 1350 within a variance of approximately 0.2 mm, centering a 1 mm×1 mm field of view of camera 1332 on the expected location of the desired feature will include the feature in the image. Image recognition software executed in control system 1320 can then find the position of the feature to within a few microns. Repeating the alignment process with a feature in another location on wafer 1350 can accurately find the position and orientation of features on wafer 1350. If stage 1340 is accurate enough, system 1300 can find any point on wafer 1350 within a few microns simply by controlling the settings of stage 1340. If stage 1340 is not sufficiently accurate, the pattern recognition is repeated at subsequent measurement points for fine adjustments at or near measurement points. When the position and orientation of wafer have been accurately identified, inspection or measurement of wafer 1350 can be performed.

Figure 11:
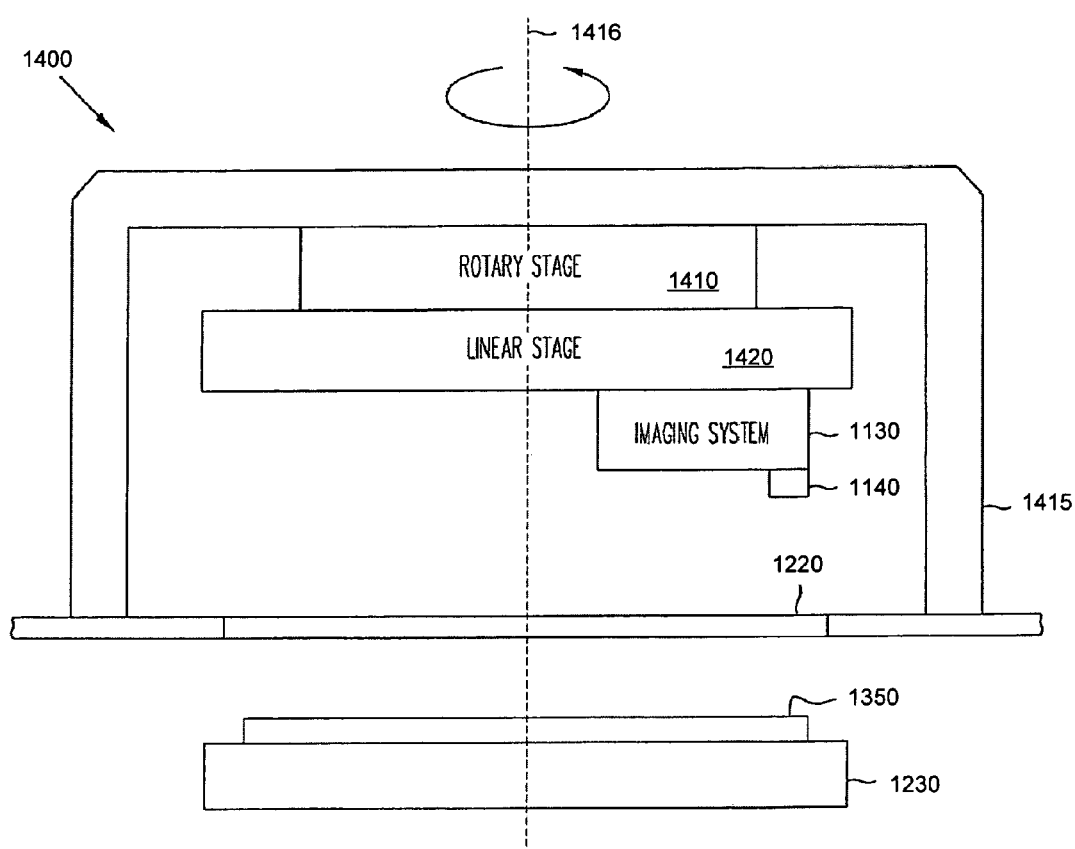
FIG. 11 shows a side views of a metrology/inspection system having a rotary stage with a rotation axis over a window.

FIG. 11 illustrates a metrology/inspection system 1400 in accordance with another embodiment of the invention. System 1400 includes a rotary stage 1410 and a linear stage 1420 that are mounted on a support structure 1415, above an optical window 1220. A rotation axis 1416 of rotary stage 1410 intersects and may be centered on optical window 1220. Imaging system 1130 is on linear stage 1410, and the combined motion of rotary stage 1410 and linear stage 1420 can position objective 1140 over any point on a wafer 1350 that may have an arbitrary orientation on station 1230.

System 1400 has the advantage of being compact when compared to a similar system that has imaging system 1130 on an X-Y stage.

Although the invention has been described with reference to particular embodiments, the description is only an example of the invention's application and should not be taken as a limitation. In particular, even though much of the preceding was aimed at systems using imaging systems that are optical microscopes, alternative embodiments of this invention include other imaging systems such as electron-beam microscopes. Various other adaptations and combinations of features of the embodiments disclosed are within the scope of the invention as defined by the following claims.

We claim:

1. A method for inspecting a wafer, comprising:
   positioning a wafer at a fixed station;
   aligning an optical system to the wafer, wherein aligning comprises: moving the optical system rotationally as required to locate an edge of the wafer; and moving the optical system to follow the edge of the wafer and locate an alignment feature on the edge of the wafer while the wafer is held linearly and rotationally stationary on the fixed station;
   moving the optical system relative to the wafer to inspect a plurality of separate inspection areas on the wafer; and
   storing a position of the optical system relative to the wafer while inspecting a plurality of separate inspection areas on the wafer.

2. The method of claim 1, wherein:
   the fixed station is inside a processing apparatus; and
   the optical system views the wafer from outside the processing apparatus, through an optical window in the processing apparatus.

3. The method of claim 1, further comprising:
   imaging each of the inspection areas using the optical system; and
   rotating images formed by the optical system, wherein each image is rotated by an amount that depends on an orientation of the wafer.

4. The method of claim 3, wherein each image is rotated by a different amount according to the orientation of the optical system when the optical system forms the image.

5. The method of claim 4, further comprising changing a rotation angle of the image from the optical system while moving the optical system, wherein the changing is such that orientation of features in the image remain constant as the optical system moves.

6. The method of claim 1, wherein the optical system is mounted on a stage and moving the optical system relative to the wafer to inspect a plurality of separate inspection areas on the wafer comprises:
   rotating a portion of the stage about a rotation axis of the stage until a linear axis of the stage crosses through a center of a first of the inspection areas; and
   moving a portion of the stage along the linear axis of the stage until a distance from the rotation axis of the stage to an objective of the optical system is equal to a distance from the rotation axis of the stage to the center of the first of the inspection areas.

7. The method of claim 1, wherein aligning the optical system further comprises measuring reflectance of the wafer and locating the edge of the wafer from a drop in the reflectance.

8. The method of claim 1, wherein after locating the alignment feature on the edge of the wafer, aligning the optical system further comprises processing an image of an area of the wafer using an image recognition module to more precisely determine the orientation of the wafer.

9. The method of claim 1, further comprising measuring film thickness at the plurality of inspection areas on the wafer.

10. A method for inspecting a wafer, comprising:
    holding the wafer in a stationary position;
    moving an optical system rotationally relative to the wafer, wherein the rotational movement of the optical system permits the optical system to inspect a plurality of separate inspection areas on the wafer without moving the wafer;
    locating an alignment feature on the edge of the wafer, wherein locating the alignment feature comprises moving the optical system to locate an edge of the wafer, and moving the optical system rotationally to follow the edge of the wafer; and
    storing a position of the optical system relative to the wafer while inspecting a plurality of separate inspection areas on the wafer.

11. The method of claim 10, further comprising:
    moving the optical system laterally relative to the wafer, wherein the rotational movement and lateral movement of the optical system permits the optical system to inspect a plurality of separate inspection areas on the wafer without moving the wafer; and
    wherein locating the alignment feature comprises moving the optical system to locate an edge of the wafer, and moving the optical system rotationally and laterally to follow the edge of the wafer.

12. The method of claim 10, wherein holding the wafer at a stationary position comprises positioning the wafer on a stationary structure.

13. The method of claim 10, further comprising:
    imaging each of the inspection areas using the optical system; and
    rotating images formed by the optical system, wherein the images are rotated by an amount based on the rotational movement of the optical system relative to the wafer.

14. The method of claim 10, wherein moving an optical system rotationally relative to the wafer is performed by rotating an objective lens in the optical system about a rotational axis that does not pass through the objective lens.

15. The method of claim 10, wherein locating an alignment feature comprises:
    measuring reflectance of the wafer; and
    determining a drop in reflectance to locate the alignment feature.

16. A method for inspecting a wafer with an optical system, the method comprising:
    providing lateral movement of the optical system with respect to the wafer;
    providing relative rotational movement between the optical system and the wafer, wherein the lateral movement and rotational movement permits the optical system to inspect a plurality of separate inspection areas on the wafer;
    generating an image signal of at least one inspection area on the wafer using the optical system; and
    processing the image signal to produce a rotated image of an inspection area based on the relative angular orientation of the optical system with the wafer.

17. The method of claim 16, wherein images of different inspection areas are rotated by a different amount based on the respective relative angular orientation of the optical system with the wafer for each image.

18. The method of claim 16, further comprising changing a rotation angle of the image produced by the optical system when there is relative rotational movement between the optical system and the wafer, wherein the act of changing is such that the orientation of features in the image remains constant.

19. The method of claim 16, wherein providing relative rotational movement between the optical system and the wafer is performed by rotating an objective lens in the optical system about a rotational axis that does not pass through the objective lens.

20. A method comprising:

providing relative lateral movement between an optical system and a wafer;

providing relative rotational movement between the optical system and the wafer, wherein the rotational movement changes a relative angular orientation of the wafer with respect to the optical system, and wherein the lateral movement and rotational movement permits the optical system to inspect a plurality of separate areas on the wafer,;

generating an image signal of at least one area on the wafer using the optical system; and processing the image signal of the area on the wafer based on the relative angular orientation of the wafer with respect to the optical system to display a rotated image that preserves a desired orientation of the wafer.

* * * * *